(12) United States Patent
Carrieri et al.

(10) Patent No.: US 8,514,392 B1
(45) Date of Patent: Aug. 20, 2013

(54) SPECTROPHOTOPOLARIMETER SENSOR AND ARTIFICIAL NEURAL NETWORK ANALYTICS FOR DISTANT CHEMICAL AND BIOLOGICAL THREAT DETECTION

(75) Inventors: Arthur H. Carrieri, Abingdon, MD (US); Jack Copper, Pittsburgh, PA (US); David J. Owens, Kingsville, MD (US); Erik S. Roese, Baltimore, MD (US); Jerold R. Bottiger, Aberdeen, MD (US); Kevin C. Hung, Baltimore, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 893 days.

(21) Appl. No.: 12/683,154

(22) Filed: Jan. 6, 2010

(51) Int. Cl.
*G01J 3/447* (2006.01)
(52) U.S. Cl.
USPC .......................... 356/322; 356/246; 356/338
(58) Field of Classification Search
USPC .............. 356/322, 246, 338, 367, 51; 706/25
See application file for complete search history.

(56) References Cited

U.S. PATENT DOCUMENTS 7,038,789 B1 * 5/2006 Carrieri .......................... 356/491

* cited by examiner

*Primary Examiner* — Tarifur Chowdhury
*Assistant Examiner* — Abdullahi Nur
(74) *Attorney, Agent, or Firm* — Ulysses John Biffoni

(57) ABSTRACT

A system, apparatus, and method of generating Stokes vectors, a Mueller matrix, and polarized scattering from an aerosol aggregate includes providing an incident infrared laser beam; causing the incident infrared laser beam to be polarization-modulated using variable stress/strain birefringence imposed on a ZnSe crystal; defining a Stokes vector associated with the incident infrared laser beam; scattering the incident infrared laser beam from an aggregate aerosol comprising interferents and analyte particles; producing a scattered-beam reactant Stokes vector by causing the scattered incident infrared laser beam to be polarization-modulated; generating a Mueller matrix by taking a transformation of the Stokes vector; and identifying the analyte using the Mueller matrix. The Mueller matrix may comprise M-elements that are functions of a wavelength of the infrared laser beam, backsattering orientation of the infrared laser beam, and a shape and size of the interferents and analyte particles.

22 Claims, 7 Drawing Sheets

Stokes vector of EM field wavefronts:
$S = (s_0, s_1, s_2, s_3)^T$ where:
$s_0 = a_1^2 + a_2^2$
$s_1 = a_1^2 - a_2^2$
$s_2 = 2a_1 a_2 \cos(\delta_2 - \delta_1)$
$s_3 = 2a_1 a_2 \sin(\delta_2 - \delta_1)$ real amplitudes $a_1$, $a_2$
and phases $\delta_1$, $\delta_2$ Mueller matrix $$\begin{pmatrix} s_0 \\ s_1 \\ s_2 \\ s_3 \end{pmatrix}_s = \begin{bmatrix} m_{11}(\theta,\varphi,d,\lambda) & m_{12}(\theta,\varphi,d,\lambda) & m_{13}(\theta,\varphi,d,\lambda) & m_{14}(\theta,\varphi,d,\lambda) \\ m_{21}(\theta,\varphi,d,\lambda) & m_{22}(\theta,\varphi,d,\lambda) & m_{23}(\theta,\varphi,d,\lambda) & m_{24}(\theta,\varphi,d,\lambda) \\ m_{31}(\theta,\varphi,d,\lambda) & m_{32}(\theta,\varphi,d,\lambda) & m_{33}(\theta,\varphi,d,\lambda) & m_{34}(\theta,\varphi,d,\lambda) \\ m_{41}(\theta,\varphi,d,\lambda) & m_{42}(\theta,\varphi,d,\lambda) & m_{43}(\theta,\varphi,d,\lambda) & m_{44}(\theta,\varphi,d,\lambda) \end{bmatrix} \begin{pmatrix} s_0 \\ s_1 \\ s_2 \\ s_3 \end{pmatrix}_i$$

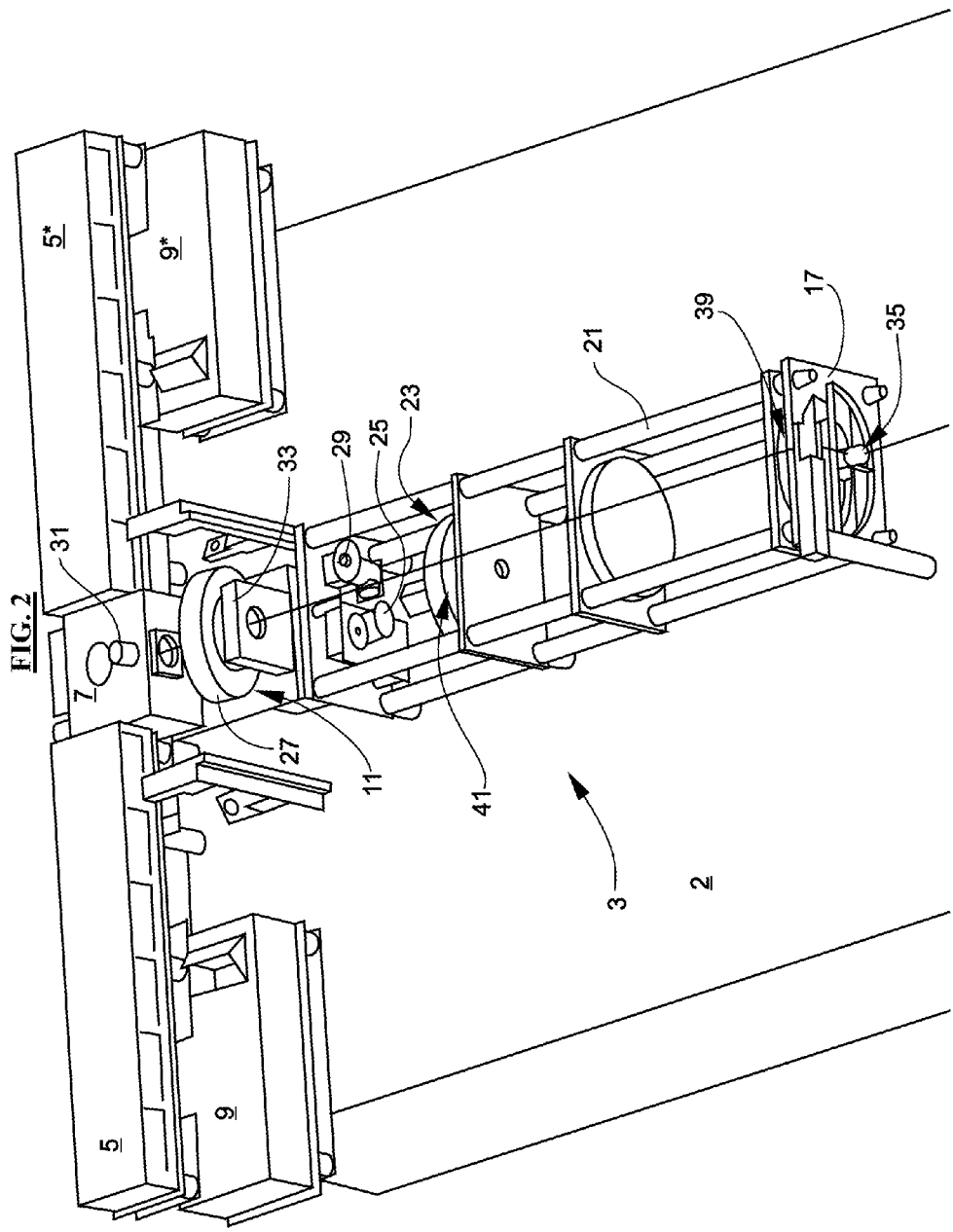

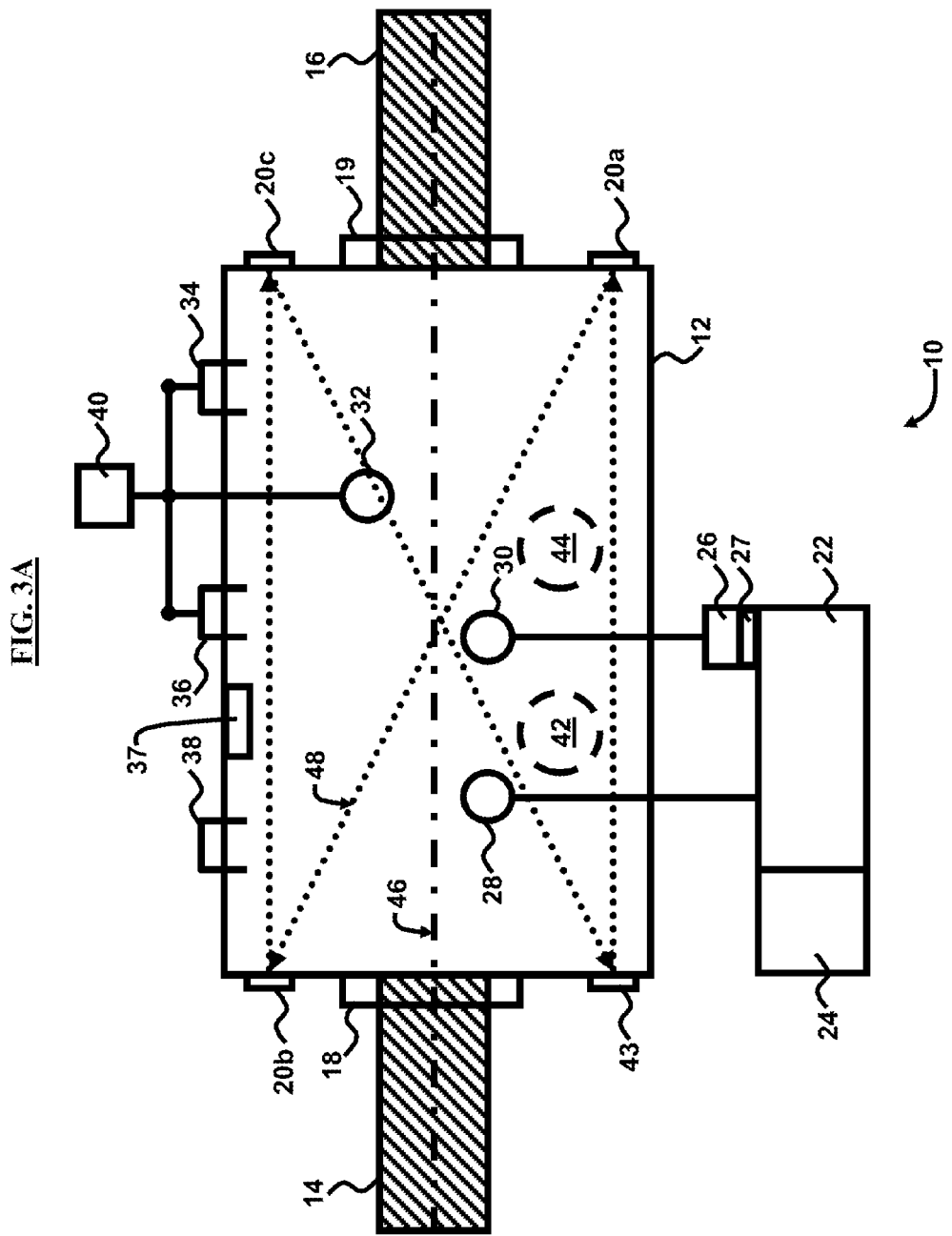

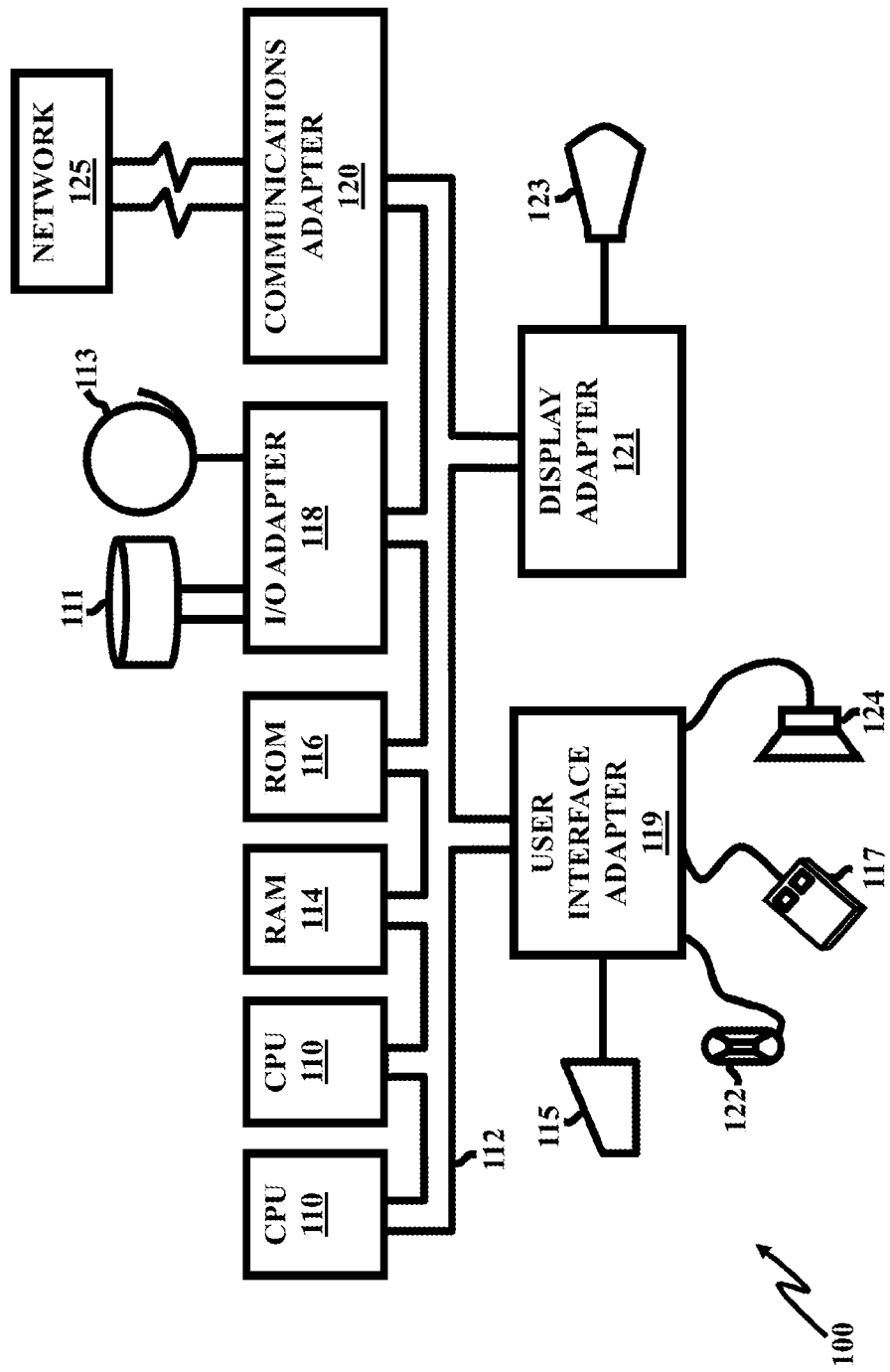

SPECTROPHOTOPOLARIMETER SENSOR AND ARTIFICIAL NEURAL NETWORK ANALYTICS FOR DISTANT CHEMICAL AND BIOLOGICAL THREAT DETECTION

GOVERNMENT INTEREST

The invention described herein may be manufactured, used, and/or licensed by or for the United States Government.

BACKGROUND

1. Technical Field

The embodiments herein generally relate to sensor technology and neural network analytics, and, more particularly, to an active spectrophotopolarimeter sensor and support system developed for distant chemical and biological aerosol identification and standoff detection.

2. Description of the Related Art

The potential for widespread injury, infection, and even death from an accidental or deliberate release of toxic chemical-biological (CB) material into the open atmosphere is exacerbated by the fact that lethal agent compounds disperse rapidly once aerosolized via detonated munitions, for instance, then settle onto land. Warfare agent material can disable, disfigure, and kill at slight concentrations and in relatively short time-frames of release. Current practices largely rely on precursor events to take action against the threat. Responses to terrorist-triggered incidents may not be recognized until impairment of human activity or, in extreme predicaments, loss of life is imminent. Clearly, a need for the rapid and true identification of CB agents and their derivatives in the ambient environment at safe distances (standoff detection) is urgent. A successful standoff detection technology provides the needed logistics for forming a first line of defense in situ and in real-time; viz, less than the human reaction time.

SUMMARY

In view of the foregoing, an embodiment herein provides an active spectrophotopolarimeter sensor and support system for distant chemical and biological aerosol and surface contamination standoff detection comprising a grating-tunable, continuous-wave, linearly polarized, $CO_2$ laser system producing beam outputs comprising an isotopic admixture of $CO_2$ gas in a gain medium of a laser providing a wider tunable bandwidth of a spectrophotopolarimeter sensor and double spectral selectivity; an optomechanical switch that produces an alternate square-wave train of incident beam pulses as output, measures power of the beam outputs when directed to an internal detector, and determines a wavelength of beams when directed to a pair of optical spectrum analyzers; a coupled transmitter linear polarizer and photoelastic modulator optic pair (POL-PEM) with 45° alignment of axes, mated to a precision rotary stage with computer-driven stepper motor control, and operating on irradiance from the incident beam pulses; telescope spider and mirror mounts that direct the alternate square-wave train of incident beam pulses onto an aerosol aggregate; a collimator and telescopic receiver in a Cassegrain style operatively connected to the telescope spider and mirror mounts; a coupled receiver photoelastic modulator and linear polarizer optic pair (PEM-POL) with 45° alignment of axes, mated to a precision rotary stage with computer-driven stepper motor control, and operating on backscattering beam outputs; a variable neutral density filter disk with belt-driven servo feedback control for regulation of backscattered radiances; and a parabolic mirror focusing collimated radiance of beam outputs onto a cooled HgCdTe photoconductive chip detector. Preferably, the chip detector is cooled at a liquid nitrogen temperature of approximately 77K.

Another embodiment provides an apparatus for dissemination, confinement, and size/concentration measurements of aerosols comprising a bioaerosol, the apparatus comprising an enclosed chamber comprising the aerosols; a pair of entrance/exit apertures comprising shutters that open/close the apertures; an aerosol intake port operatively connected to the chamber; an aerodynamic particle sizer operatively connected to the aerosol intake port; a high-pressure ejection nozzle operatively connected to the chamber; a hopper and aerosol reservoir that provides powder samples to the chamber through the nozzle; a plurality of conduits that control aerosol movement to/from the chamber; a vacuum switch operatively connected to the plurality of conduits, wherein the vacuum switch controls exhaust of the bioacrosol from the chamber via the plurality of conduits; and a chamber vacuum cleaner operatively connected to the chamber.

The apparatus may further comprise a spectrophotopolarimeter comprising a sensor receiver; a system that aligns the spectrophotopolarimeter to the chamber, inspects a uniformity of a dispersed aerosol sample inside the chamber, and measures a particle size distribution and concentration of a sampling plume of the bioaerosol; a visible HeNe laser beam on-axis of the sensor receiver; a plurality of flat mirrors aligned outside opposing walls of the chamber, wherein the mirrors reflect the visible HeNe laser beam in a Z-pattern for direct inspection of particle scattering and vertical aerosol density; and a console system operatively connected to the aerodynamic particle sizer that processes and displays statistics of the bioacrosol. Additionally, the apparatus may further comprise an inner tube aligned with the pair of entrance/exit apertures; and a vapor mist concentration generator positioned within the chamber and aligned with the inner tube. In one embodiment, the chamber is windowless.

Moreover, the plurality of conduits may comprise a low vacuum conduit used prior to high-efficiency particulate air (HEPA) filtration of the chamber for containment of the bioaerosol within the chamber; a first high vacuum conduit used prior to the HEPA filtration of the chamber for evacuation of the bioaerosol; and a second high vacuum conduit used subsequent to HEPA filtration for ventilation of the chamber. Additionally, the apparatus may further comprise a pair of gloves operatively insertable inside the chamber and used for washing the inside of the chamber.

The spectrophotopolarimeter may comprise a grating-tunable, continuous-wave, linearly polarized, $CO_2$ laser system producing beam outputs comprising an isotopic admixture of $CO_2$ gas in a gain medium of a laser providing a wider tunable bandwidth of a spectrophotopolarimeter sensor and double spectral selectivity; an optomechanical switch that produces an alternate square-wave train of incident beam pulses as output, measures power of the beam outputs when directed to an internal detector, and determines a wavelength of beams when directed to a pair of optical spectrum analyzers; a coupled transmitter linear polarizer and photoelastic modulator optic pair (POL-PEM) with 45° alignment of axes, mated to a precision rotary stage with computer-driven stepper motor control, and operating on irradiance from the incident beam pulses; a telescope spider and mirror mounts that direct the alternate square-wave train of incident beam pulses onto an aerosol aggregate; and a collimator and telescopic receiver in a Cassegrain style operatively connected to the telescope spider and mirror mounts.

Also, the spectrophotopolarimeter may further comprise a coupled receiver photoelastic modulator and linear polarizer optic pair (PEM-POL) with 45° alignment of axes, mated to a precision rotary stage with computer-driven stepper motor control, and operating on backscattering beam outputs; a variable neutral density filter disk with belt-driven servo feedback control for regulation of backscattered radiances; and a parabolic mirror focusing collimated radiance of beam outputs onto a cooled HgCdTe photoconductive chip detector. Preferably, the chip detector is cooled at a liquid nitrogen temperature of approximately 77K. Furthermore, the apparatus may comprise a computerized artificial neural network model developed based on the statistics of the bioaerosol as a classifier database of aerosol aggregates. In one embodiment, the artificial neural network model comprises a hybrid Kohonen self-organizing map (SOM) feed-forward artificial neural network model.

Another embodiment provides a method of generating Stokes vectors, a Mueller matrix, and polarized scattering from an aerosol aggregate, the method comprising providing an incident infrared laser beam: causing the incident infrared laser beam to be polarization-modulated using variable stress/strain birefringence imposed on a ZnSe crystal; defining a Stokes vector associated with the incident infrared laser beam; scattering the incident infrared laser beam from an aggregate aerosol comprising interferents and analyte particles; producing a scattered-beam reactant Stokes vector by causing the scattered incident infrared laser beam to be polarization-modulated; generating a Mueller matrix by taking a transformation of the Stokes vector; and identifying the analyte using the Mueller matrix. The Mueller matrix may comprise M-elements that are functions of a wavelength of the infrared laser beam, backsattering orientation of the infrared laser beam, and a shape and size of the interferents and analyte particles.

The method may further comprise directing a pair of continuous-wave $CO_2$ laser beams into entrance ports of an optical switching device, wherein an output of the optical switching device comprises an alternate square-wave sequence of equal intensity laser beams; directing the equal intensity laser beams into optical spectrum analyzers for wavelength determination; directing the equal intensity laser beams through a coupled linear polarizer-then-photoclastic modulation (POL-PEM) optics unit; and confining a temporal transverse electromagnetic wave of the equal intensity laser beams to a given geometric plane to establish a Stokes vector associated with a polarization state of the equal intensity laser beams. Additionally, the method may further comprise modulating the Stokes vector via periodic stress/strain birefringence transduction; creating a polarization-modulated laser beam from the POL-PEM optics unit; reflecting the polarization-modulated laser beam twice 90° using flat mirrors; directing the reflected laser beam into an aerosol chamber comprising entrance and exit apertures centered on-axis with a spectrophotopolarimeter receiver; and collecting backscattered radiance of the reflected laser beam scattered from the bioaerosols using a coupled linear photoelastic-then-polarizer modulation (PEM-POL) optics unit.

Moreover, the method may further comprise splitting a portion of the equal intensity laser beams into a power meter head unit. Also, the method may further comprise developing an artificial neural network model based on the identified analyte as a classifier database of aerosol aggregates. In one embodiment, the artificial neural network model comprises a hybrid Kohonen SOM feed-forward artificial neural network model.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 2 is a schematic diagram illustrating a differential-absorption Mueller matrix spectroscopy (DlAMMS) sensor according to the embodiments herein;

FIG. 3A is a schematic diagram illustrating an aerosol chamber test apparatus according to the embodiments herein;

FIG. 6 is a schematic diagram illustrating a computer architecture used in accordance with the embodiments herein.

DETAILED DESCRIPTION OF PREFERRED EMBODIMENTS

Figure 1:
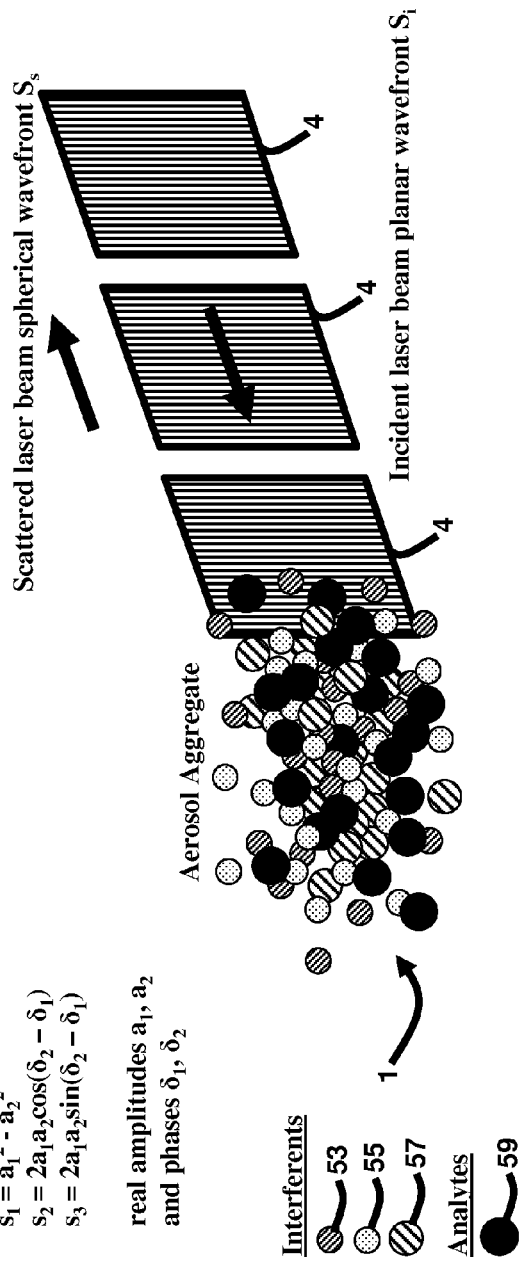
FIG. 1 is a schematic diagram illustrating Stokes vectors, a Mueller matrix, and polarized scattering from an aerosol aggregate according to the embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

According to the embodiments herein, an aerosol aggregate is interrogated by multiple $CO_2$ laser beams spanning the middle infrared region where the subject analyte is molecularly vibration-active. Incident irradiance and backscatter radiance of the beams are distinctly polarization-modulated for electronic acquisition of the Mueller matrix and building of a core database. The database is a resource of input data fields for training and validating hybrid Kohonen, self-organizing map feed-forward artificial neural network models that serve pattern recognition and classification roles. The best performance networks mathematically cluster analyte, interferent, and control plumes accurately with near overlap of aerosol classes. Referring now to the drawings, and more particularly to FIGS. 1 through 6, where similar reference characters denote corresponding features consistently throughout the figures, there are shown preferred embodiments.

Stokes Vector, Mueller Matrix, and Detection Application

For ease of understanding, notations of vectors are designated in italics below. From classical field theory, consider a transverse electromagnetic wave (TEMW) propagating in direction $k=kn=2\pi n/\lambda$ with field vector E of mathematical form:

$$E(x,t)=(\epsilon_1 E_1+\epsilon_2 E_2)e^{i(k\cdot x-\omega t)} \quad (1)$$

where k is wavevector, n is its unit normal vector, $\lambda$ is wavelength. $\omega=2\pi\upsilon$ is circular frequency, and $\upsilon$ linear frequency of oscillation, t is time of propagation, x is field position, $\epsilon_1$ and $\epsilon_2$ are orthogonal unit basis vectors in the reference frame of TEMW, and the complex field amplitudes along those basis vectors are:

$$E_1=a_1 e^{i\delta_1}, E_2=a_2 e^{i\delta_2} \quad (2)$$

with real amplitudes ($a_1$, $a_2$) and phases ($\delta_1$, $\delta_2$). Now consider E(x,t) representing the TEMW of an infrared laser beam onto aerosol aggregate 1 as depicted in FIG. 1. A Stokes vector is constructed by the parameterization of E(x,t) amplitudes and phases by defining relationships:

$$s_0 \equiv |\epsilon_1 \cdot E|^2+|\epsilon_2 \cdot E|^2 = a_1^2+a_2^2 \quad (3a)$$

$$s_1 \equiv |\epsilon_1 \cdot E|^2-|\epsilon_2 \cdot E|^2 = a_1^2-a_2^2 \quad (3b)$$

$$s_2 \equiv 2Re[(\epsilon_1 \cdot E)^*(\epsilon_2 \cdot E)] = 2a_1 a_2 \cos(\delta_2-\delta_1) \quad (3c)$$

$$s_3 \equiv 2Im[(\epsilon_1 \cdot E)^*(\epsilon_2 \cdot E)] = 2a_1 a_2 \sin(\delta_2-\delta_1) \quad (3d)$$

where asterisk (*) signifies a complex conjugation, the dot symbol (·) denotes the inner product of basis and electric field vectors, paired vertical bars designate modulus or absolute value of the inner product complex number, and Re/Im represent real/imaginary components of their respective arguments. The M-matrix is a 4×4 transformation of incident laser beam 1×4 Stokes vector $s_i=(s_0, s_1, s_2, s_3)_i^T$ into the scattered beam Stokes vector $s_s=(s_0, s_1, s_2, s_3)_s^T$ accordingly: $s_s=Ms_i$; where superscript T designates transposition. M can be derived by linking algebras of Pauli and Jones accordingly:

$$M_{ij}=\tfrac{1}{2}tr\ \sigma_i J\sigma_j J^\dagger \quad (4)$$

where J is the complex Jones matrix; $\sigma_i$, $\sigma_j$ are real Pauli matrices; tr denotes trace of matrix product; and the dagger symbol represents Hermitian transposition. Substitution and factorization yield the elegant Jones representation of M.

$$M = \frac{1}{2} \begin{pmatrix} |J_{||||}|^2+|J_{|| \perp}|^2+|J_{\perp ||}|^2+|J_{\perp \perp}|^2 & |J_{||||}|^2-|J_{|| \perp}|^2+|J_{\perp ||}|^2-|J_{\perp \perp}|^2 & 2Re(J_{||||}J_{|| \perp}^*+J_{\perp \perp}J_{\perp ||}^*) & 2Im(J_{||||}J_{|| \perp}^*-J_{\perp \perp}J_{\perp ||}^*) \\ |J_{||||}|^2+|J_{|| \perp}|^2-|J_{\perp ||}|^2-|J_{\perp \perp}|^2 & |J_{||||}|^2-|J_{|| \perp}|^2-|J_{\perp ||}|^2+|J_{\perp \perp}|^2 & 2Re(J_{||||}J_{|| \perp}^*-J_{\perp \perp}J_{\perp ||}^*) & 2Im(J_{||||}J_{|| \perp}^*+J_{\perp \perp}J_{\perp ||}^*) \\ 2Re(J_{||||}J_{\perp ||}^*+J_{\perp \perp}J_{|| \perp}^*) & 2Re(J_{||||}J_{\perp ||}^*-J_{\perp \perp}J_{|| \perp}^*) & 2Re(J_{||||}J_{\perp \perp}^*+J_{|| \perp}J_{\perp ||}^*) & 2Im(J_{||||}J_{\perp \perp}^*-J_{|| \perp}J_{\perp ||}^*) \\ -2Im(J_{||||}J_{\perp ||}^*-J_{\perp \perp}J_{|| \perp}^*) & -2Im(J_{||||}J_{\perp ||}^*+J_{\perp \perp}J_{|| \perp}^*) & -2Im(J_{||||}J_{\perp \perp}^*+J_{|| \perp}J_{\perp ||}^*) & 2Re(J_{||||}J_{\perp \perp}^*-J_{|| \perp}J_{\perp ||}^*) \end{pmatrix} \quad (5)$$

M-elements carry functional dependencies on geometric particle shape and size of scatterer (bundled variables denoted as symbol d in FIG. 1) and its spectroscopy is derived from the complex refractive index $N=\eta(\lambda)+i\xi(\lambda)$. Real and imaginary components of N are nonlinear variables in the neighborhood of resonant absorption of a beam by the aerosol aggregate 1, whereby $d\xi(\lambda)/d\lambda \equiv \xi(\lambda)=0$. An evanescence phase change is manifest in $s^a_s$ (superscript a=absorptive) at the peak absorption beam cross section relative to phase conservation in $s^n_s$ (superscript n=nonabsorptive) at the resonance tail where $N \approx \eta(\lambda)$. A DIAMMS sensor 3 (of FIG. 2) identifies the analyte by discerning contrasts between $s^a_s$ and $s^n_s$; i.e., sets of susceptible differential-absorption M-elements are associated to the analyte and vice versa (one-to-one). Artificial neural network technology is the preferred embodiment for mappings of M-elements into detection events or non-events.

In FIG. 1, Stokes vectors, a Mueller matrix, and polarized scattering from an aerosol aggregate 1 are depicted. Stacked rectangular objects 4 depict the electromagnetic field wavefronts (surfaces of exact constant phase) of an incident infrared laser beam moving right-to-left onto the aerosol aggregate 1 (direction of arrow inside rectangle 4). The beam is polarization-modulated via variable stress birefringence imposed on a ZnSc crystal. The incident beam of defined Stokes vectors $s_i$ scatters from aerosol aggregate 1 comprising interferents 53, 55, 57 and analyte 59 particles producing a scattered-beam reactant Stokes vector $s_s$ whose wavefronts are of constant phase propagating away from aerosol aggregate 1, which is distinctly polarization-modulated a second time. The Mueller matrix is the transformation of Stokes vectors, and its elements (M-elements) are generally functions of beam wavelength ($\lambda$), polar ($\theta$), and azimuth ($\phi$) orientations, and particle shape and size (d). The embodiments herein focus on backscattering ($\theta i=\theta s$, $\phi_i=\phi_s$). The polarization modulation of incident and scattered beam wavefronts encode $s_s$ for electronic measurement of all 16 M-elements. Those M-elements exhibiting susceptible behaviors by the analyte 59, as it is driven in to and out of molecular vibration resonance by probing beams, provide a foundation for the identification and standoff detection of that analyte 59.

Detection System and Calibration

FIG. 2, with reference to FIG. 1, illustrates a differential-absorption Mueller matrix spectroscopy (DIAMMS) sensor 3 according to the embodiments herein. Furthermore, components 5, 5* are coherent select-50 grating-tunable, continuous-wave, linearly polarized, $CO_2$ laser systems, where the asterisk signifies an isotopic admixture of $CO_2$ gas in the gain medium, which provides a slightly wider tunable bandwidth of sensor and doubles spectral selectivity. An optomechanical switch 7 produces an alternate square-wave train of incident beam pulses to the aerosol aggregate 1 of FIG. 1, measures power of dual beams, and determines wavelengths via the sending of beams to optical spectrum analyzers 9, 9*. A POL-PEM: transmitter linear polarizer and photoelastic modulator optic pair 11, mated to precision rotary stage 33 with computer-driven stepper motor control, operates on irradiance from incident beams. The sensor 3 further comprises a spider and mirror mount 17, and a collimator and telescopic receiver 21 A PEM-POL: receiver photoelastic modulator and linear polarizer optic pair 23, mated to its precision rotary stage, operates on condensed and collimated radiance of backscattering beams. A variable neutral density filter disk 25 with belt-driven servo feedback control is provided for regulation of backscattered radiance. Moreover, a parabolic mirror (not visible in the view provided in FIG. 2, but positioned proximate to disk 25 and detector 29) is used for focusing collimated radiance of beams onto a 1×1 mm HgCdTe photoconductive chip detector 29 cooled at a liquid nitrogen temperature of approximately 77K.

The dual continuous-wave $CO_2$ laser beams 5, 5\* (the asterisk implies laser with isotopic $C^{14}O_2$ gain medium) are directed into entrance ports of the optical switching device 7 whose output is an alternate square-wave sequence [ . . . 5:5\* . . . ]$_{transmit}$ of equal intensity beams. Moreover, the device 7 directs **5 (5\*) into optical spectrum analyzers 9 (9\*) for wavelength determinations, and splits a small fraction of [ . . . 5:5\* . . . ]$_{transmit}$ into power meter head 31. Upon exiting the device 7, [ . . . 5:5\* . . . ]$_{transmit}$ is directed through coupled linear polarizer-then-photoelastic modulation optics (POL-PEM) 11 mounted to precision rotary stage 33**. The POL confines the temporal TEMW E-field vector to a given plane and establishes $s_i$. The PEM then polarization-modulates $s_i$ via periodic stress/strain birefringence transduction whose mechanism is described below.

The orthogonal E-field components of TEMW incident to the front surface of PEM birefringent ZnSe crystal are aligned such that components of equal amplitude traverse extra-ordinary and ordinary axes in the crystalline structure by virtue of a 45° alignment between axes of POL-PEM optics. The phase in the traveling extra-ordinary TEMW component undulates as $\delta_2 = \delta_{20} \cos(\upsilon_m)$ as natural mechanical resonance in the (cleaved and antireflection-coated) ZnSe crystal is driven via tuned piezoelectric stress compression-relaxation acting across opposing ends of the crystal (transduction), where $\delta_{20}$ is the peak phase retardation and $\upsilon_m$ is the modulation frequency of the transducer. The traveling orthogonal ordinary component of TEMW is unaltered in phase. Ordinary and extra-ordinary E-field components in and out of phase with each other combine at the exiting surface of ZnSe PEM crystal transforming linearly-polarized $s_i$ into a continuum of left- and right-linear/elliptical/circular polarization states.

The subject aerosol aggregate 1 reacts to one continuum polarization cycle in 27.03 µs (transmitter PEM modulates at 37 kHz) ad interim and ad fin. The incident polarization-modulated beams $[\ldots \mathbf{5}{:}\mathbf{5}^* \ldots]_{transmit}$ are next reflected twice by 90° by flat mirrors (not visible in the view provided in FIG. 2, but proximate to position 39 behind the spider 17 as well as position 35 in the center of spider 17), with a latter mirror 35 mounted onto spider 17, and then the beams $[\ldots \mathbf{5}{:}\mathbf{5}^* \ldots]_{transmit}$ are directed through aerosol chamber 12 (of FIG. 3A) with entrance-exit apertures 14, 16 centered on-axis of the spectrophotopolarimeter receiver (the receiver comprising primary telescope spherical mirror 35, secondary Cassegrain telescope spherical mirror (i.e., near position 39)) a 10× condenser optic 21 in the style of a Cassegrain telescope—second mated PEM-then-POL pair 23, variable neutral density filter wheel 25, 90° parabolic mirror 27, and cryogenic detector 29 whose 1×1 $mm^2$ HgCdTe photoconductive chip is on focus of mirror 27. As in the transmitter, the PEM-POL group 23 is axially aligned 45° and permuted by its rotary stage (not clearly visible in the view provided in FIG. 2, but proximate to position 41) in accordance to M-elements data acquisition protocol. The receiver PEM modulates at 39 kHz, a 2 kHz offset from the transmitter PEM. A conversion of dual-PEM polarization modulation to intensity modulation in $s_s=Ms_i$ is a ramification of the linear polarizer optic POL in receiver PEM-POL 23. This intensity of $s_s$, received at the HgCdTe chip, is regulated via the bidirectional rotation of a variable neutral density filter wheel 25 for proper M-elements production.

The determination of the M-elements is equivalent to a lock-in detection of eight coefficients of primary and overtone frequencies in $s_s$ plus an additional phase-insensitive component. There is one and only one M-element assignment per primary/overtone frequency. Furthermore, all frequency components in $s_s$ have Bessel coefficients $J_{n,k}(\xi_0)$, where $\xi_0$ is the maximum retardation of stressed PEM crystals. The quantity $\xi_0=2.404$ radians, a null in the zero-order Bessel function $J_0(\xi_0)=0$, is held during spectral M-elements acquisitions. $J_{n,k}(\xi_0)$ are dampening coefficients in the Fourier transformation intensity functional (I) of $s_s$:

$$I = I_{dc} + I_{ac}\left(\sum_{n\neq k=0}^{2} J_n(\text{æ}_0)\cos n\acute{\imath}_1,\ J_k(\text{æ}_0)\cos k\acute{\imath}_2,\ J_n(\text{æ}_0)\cos(n\acute{\imath}_1 \pm k\acute{\imath}_2)\right) + I_{ac}^{\varepsilon}\left(\sum_{n\neq k=3}^{\infty}\left(\prod_{n,k} J_n(\text{æ}_0)J_k(\text{æ}_0)\cos n\acute{\imath}_1 \cos n\acute{\imath}_2\right)\right) \tag{6}$$

where $I_{dc}$ is phase-insensitive (scalar), $I_{ac}$ is linear phase-sensitive, and $I^{\epsilon}_{ac}$ is non-linear phase-sensitive. The high overtone $I^{\epsilon}_{ac}$ components are increasingly negligible with order n, k in $J_{n,k}(\xi_0)$. Moreover, $I^{\epsilon}_{ac}$ is suppressed by electronic filtration in the data acquisition system of a spectrophotopolarimeter, which is desirable for preventing cross-talk between the M-elements. $I_{dc}$ tracks Mueller element [1, 1] while the linear phase-sensitive intensity $I_{ac}$ with two circular frequency primaries ($\omega_1$, $\omega_2$) and six overtones ($2\omega_1$, $2\omega_2$, $\omega_1\pm\omega_2$, $\omega_1\pm2\omega_2$, $2\omega_1\pm\omega_2$, $2\omega_1\pm2\omega_2$) track eight of sixteen non-[1, 1] M-elements.

Transmitter and receiver optic groups POL-PEM:PEM-POL are permuted in four distinct 45° rotations (two permutations each between POL-PEM and PEM-POL optic groups 11 and 23 of FIG. 2) to produce a full 16-element backscattering M of aerosol aggregate 1 of FIG. 1 per beam wavelength 5, 5* of FIG. 2. The effect of permutations is reassignment of M-elements in $I_{ac}$ with degeneracy. The order of permutations is enacted within the sensor's electronics and modular $C^{++}$ code blocks that choreograph M acquisitions in sequences. Moreover, $s_s$ is called a scattergram, the set of optics POL-PEM:PEM-POL is a Mueller matrix spectrometer (MMS), and the MMS with integrated data acquisition and preprocessing system is a DIAMMS standoff identification and detection system.

Table 1 illustrates a method of spectrophotopolarimeter calibration. Known calibrator optic Ψ is inserted and rotated within the MMS engine accordingly: POL-PEMM:Ψ:PEM-POL; where axial orientations in POL-PEM (transmitter) and PEM-POL (receiver) are V(−45°) :(+45°) V, where V is vertical to the reference plane (optics table 2 in FIG. 2) and the sign convention + (−) is clockwise (counterclockwise) as viewing the laser source from the transmitter or aerosol backscattering cross-section from the receiver of sensor 3. Calibrator Ψ is a polarizer (P), a quarter-wave plate (Q), or an ordered combination thereof (QP or PQ) with one optic positioned stationary vertical while the other rotates uniformly. The calibration source beam is tuned to the 10 P(20) line of nonisotopic $CO_2$ laser, as Q and P optics are manufactured for precise ¼-wave retardation and peak extinction ratio, respectively, at 10.6 μm.

When PEMs of MMS are active and under computer control (peak retardation $\xi_0=2.404$ radians maintained for all laser beam wavelengths), the amplitude and phase inputs to each phase-sensitive detector board (channels 2 through 9) are adjusted so as to match Ψ's known M-element in rotation angle ρ. Table 1 lists the exact sinusoid functional associations per M-element.

TABLE 1

| Channel | Lock-in frequencies (kHz) | Mueller matrix element | Calibrator optic(s) and waveform | | | | |
|---|---|---|---|---|---|---|---|
| | | | POL(θ) | Q(ρ) | Q(0)Q(ρ) | POL(0)Q(ρ) | Q(ρ)POL(0) |
| 1 | dc | 1,1 | — | — | — | — | — |
| 2 | $\omega_r$ (39) | 4,1 | | | | | $-\sin2\rho$ |
| 3 | $\omega_t$ (37) | 1,4 | | | | $-\sin2\rho$ | |
| 4 | $2\omega_r$ (78) | 2,1 | $\cos2\theta$ | | | | |
| 5 | $2\omega_t$ (74) | 1,2 | $\cos2\theta$ | | | | |
| 6 | $\omega_t+\omega_r$ (76) | 4,4 | | | $\cos2\rho$ | | |
| 7 | $2\omega_t+\omega_r$ (113) | 4,2 | | $\sin2\rho$ | | | |
| 8 | $2\omega_t-2\omega_r$ (4) | 2,2 | $\cos^2 2\theta$ | | | | |
| 9 | $\omega_t+2\omega_r$ (115) | 2,4 | | $\sin2\rho$ | | | |

As indicated in Table 1, the calibration of Mueller matrix spectrometer (MMS) engine in the POL-PEM:Ψ:PEM-POL configuration is shown where POL-PEM:PEM-POL axes are V(−45°):Ψ(ρ or 0):(+45°) V with vertical (V) and ±45° orientations relative to the plane of optics table 4 (of FIG. 2) as viewing laser (in the transmitter optics) or backscattering (in the receiver optics) sources. The piezoelectric transducer frequencies of transmitter and receiver photoelastic modulation (PEM) crystals are $\omega_t$=37 kHz and $\omega_r$=39 kHz; respectively, and Ψ is the calibrator optic(s) comprising of linear polarizer POL and/or quarter-wave plate Q. Ψ=POL(0) and Q(ρ) rotate about their central axis normal to the incident laser beam. Waveforms shown are the known of Mueller matrix elements of POL(θ), Q(ρ), Q(0)Q(ρ), POL(0)Q(ρ) and Q(ρ)POL(0) as listed. Mueller matrix element [1, 1], the phase-insensitive element, is acquired separately from a split in the scattergram waveform and output by an individual lock-in detection board of the DIAMMS data acquisition system 22 (of FIG. 3A).

As an example, calibration for element [1, 4] requires Ψ(ρ)=P(0)Q(ρ): a quarter-wave plate rotating axially followed by a fixed vertical linear polarizer (they are noncommutative optics). Channel 3, a phase-sensitive detector (PSD) board, is active with transmitter PEM primary frequency 37 kHz as reference input, $s_s$ as signal input (Equation 6), and Mueller element [1, 4] as output. Calibration of this channel is complete when phase and amplitude settings on the PSD are adjusted to yield—sin 2ρ precisely, at the PSD output node. Likewise, channels 2 and 4-9 are calibrated in the sensor's data acquisition system per the matching Ψ(ρ) M-element procedure described above.

Aerosol Test Chamber

Figure 3B:
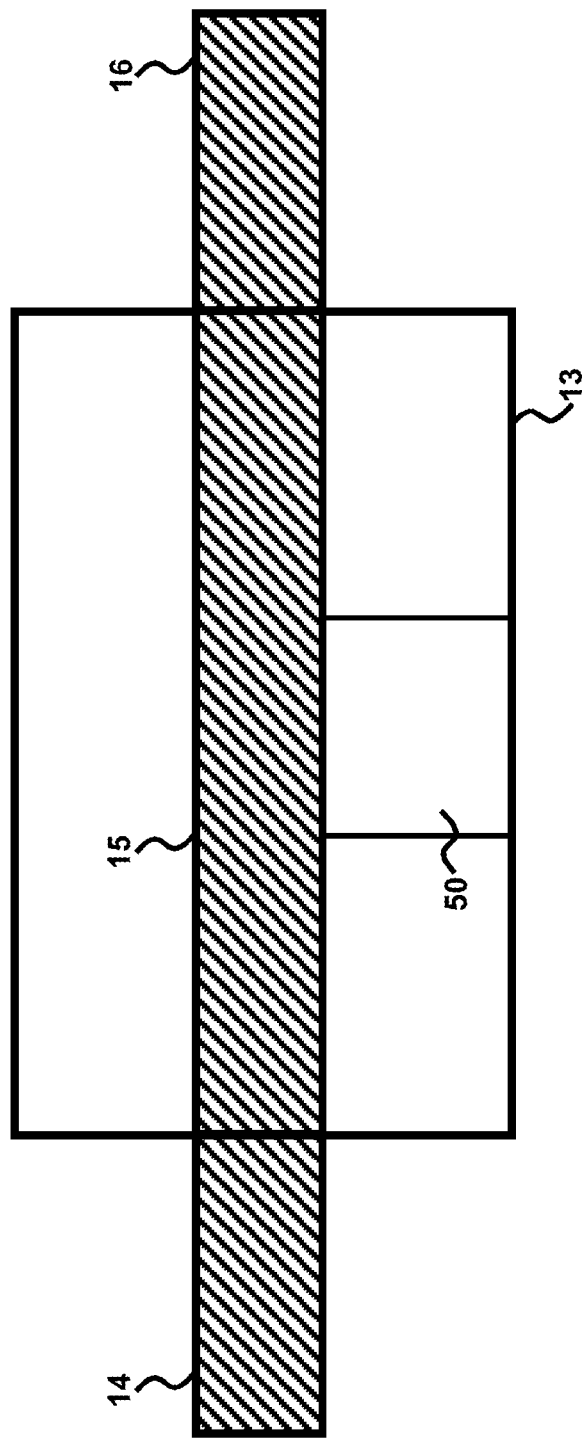
FIG. 3B is a schematic diagram illustrating another aerosol chamber test apparatus according to the embodiments herein.

FIGS. 3A and 3B, with reference to FIGS. 1 and 2, illustrate an aerosol chamber 12 and water mist chamber-within-chamber 13, respectively. In one embodiment, both chambers 12, 13 are operated windowless so as to prevent extraneous surface reflections of beams [ . . . 5:5* . . . ]$_{transmit}$ that would dominate neat M-elements signal in aerosol/mist backscatter radiance.

FIG. 3A illustrates aerosol chamber 12 and supporting system 10 for dissemination, confinement, and size/concentration measurements of nonviable biological warfare agent simulants γ-irradiated *Bacillus subtilis* and chicken egg-white albumen, interferent Arizona road dust, control talcum powders, and others. The chamber 12 comprises an extended entrance aperture 14 and shutter 18, and aerosol chamber exit aperture 16 and shutter 19. An aerosol intake port 28 is operatively connected to an aerodynamic particle sizer (APS) 22. A hopper 26 for powder sample stock and a high-pressure ejection nozzle 30 are also included. The chamber 12 further includes a low vacuum conduit 32 used before HEPA filtration for containment of aerosol. A high vacuum conduit 34 is used before HEPA filtration for evacuation of aerosol. Additionally, a high vacuum conduit 36 is used after HEPA filtration for ventilation of the chamber 12. A vacuum switch 40 is used to exhaust aerosol via conduits 32, 34, 36. A chamber vacuum cleaner 38 and a pair of gloves 42, 44 are used for chamber wash-down.

The DIAMMS sensor of FIG. 2 may be aligned to aerosol chamber 12 for inspection of uniformity of dispersed aerosol sample inside the chamber 12, and measurement of particle size distribution and concentration of sampling plume. A visible HeNe laser beam on-axis of the sensor receiver of FIG. 2 is shown as dotted line 46 in FIG. 3A. Flat mirrors 20a-20c are aligned outside of the chamber 12 reflecting visible HeNe laser beam 48 in a Z-pattern and back onto itself for direct inspections of particle scattering and thus vertical aerosol density. The HeNe laser 43 points its beam 48 left to right (in FIG. 3A). Flat mirror 20a is positioned at a predetermined angle that reflects the incident beam 48 to flat mirror 20b, which then reflects the beam 48 to flat mirror 20c, which retroreflects the beam 48 back to the laser 43. A console 24 is operatively connected to the APS 22 for display of APS aerosol statistics.

In FIG. 3A, entrance aperture 14 and exit aperture 16 are aligned to the optical axis of the sensor receiver of FIG. 2 and use shutters 18, 19 to close and open in synchronous to allow aerosol injection and beam transmissions through the chamber 12. With shutters 18, 19 closed, material is drawn from hopper 26, which is constantly agitated by an enclosed vibrating membrane 27 so as to prevent binding or lumping of powder stock, through nozzle 30 via a high-pressure line. An air ionizer 37 may be used inside the chamber 12, at times, to neutralize frictionally charged particles ejected from the tip of the nozzle 30. With the sample dispersed, shutters 18, 19 open, [ . . . 5:5* . . . ]$_{transmit}$ is backscattered from aerosol, and M-elements data collection sequences begin via menu-driven scripts. Furthermore, with the shutters 18, 19 open, a slight negative pressure inside the chamber 12 is enacted through duct 36 to contain aerosol mass between apertures 14, 16. Subsequently, ducts 34, 36, 38 ventilate a slight particle-laden laminar flow outside the chamber 12 after high efficiency particulate air (HEPA) filtration.

The APS 22 monitors the geometry and concentration of aerosol particles inside the chamber 12 when M-elements data collection sequences are on-line. A difference in inertia (lag) exhibited by various particle shapes and masses become sorted in flow through a pneumatic cell of the APS 22 via intake port 28. Two offset laser beams internal to the APS 22 focused at the exit aperture (not shown) of the APS 22 pneumatic cell are scattered by particles emanating from that APS cell in flow, and time intervals of pulses are correlated to diameters of particles in a statistical distribution. Particle statistics and M acquisitions by the spectrophotopolarimeter are synchronized by computer clocks time-stamping these disparate datasets.

As indicated above, when cleaning the chamber 12 after measurement trial(s), the ventilation is switched at switch 40 so as to draw lingering aerosol mass inside the chamber 12 outward through a HEPA filter bank (via duct 34) and outside the chamber 12 (via duct 36) as shown in FIG. 3A. Afterwards, gloves 42, 44 are used to safely wash-down and disinfect the internal walls of the chamber 12.

Furthermore, as indicated above, in FIG. 3A, the chamber 12 is illustrated prior to an aerosol M-elements data collection run and after chamber-sensor optical alignment. Visible beam 46 (of FIG. 3A), from a He-Ne laser, co-aligns entrance-exit apertures 14, 16, a laboratory exit port (not shown), and the optical axis of the spectrophotopolarimeter receiver of FIG. 2. Another visible beam, 48, crisscrosses the length and height of the interior of the chamber 12 via flat mirrors 20a-20c mounted just outside the clear chamber 12. Homogeneity of an aerosol scatterer is inspected by direct observation of scattered beam 48. These observations help balance the slight negative internal pressure of the chamber 12 discussed above. Aerosol particle number density, surface density, and mass count are recorded in computer memory (e.g., as shown in FIG. 6) along with particle size and concentration statistics. These data are inclusive of particle count medium, mean, standard deviation, geometric standard deviation, skewness, coefficient of variance, and diameter average statistics with or without log-normal distribution.

FIG. 3B illustrates a chamber-within-chamber configuration to measure all 16 Mueller matrix elements of water mist (cloud interferent). A vapor mist concentration generator 50 is positioned within the chamber 13 and connected to an inner tube 15 with ventilation apertures 14, 16 on both ends of the tube 15 and drawing sample mist (pure and impure water) to the outside of the chamber 13. FIG. 3B illustrates a configuration of aerosol chamber 13 for measuring M-elements of liquid water mist (a natural cloud interferent) over the full tunable middle infrared bandwidth of the sensor 3 of FIG. 2. A concentration of mist from source generator 50 enters midway through the chamber-within-chamber 13. A slight negative pressure held at the ends of the tube 14, 16 yields minimum laminar flow of mist from center of tube 15 outward to the ends 14, 16.

Empirical Mueller Matrix Data Fields and Neural Network Classifiers

Figure 4:
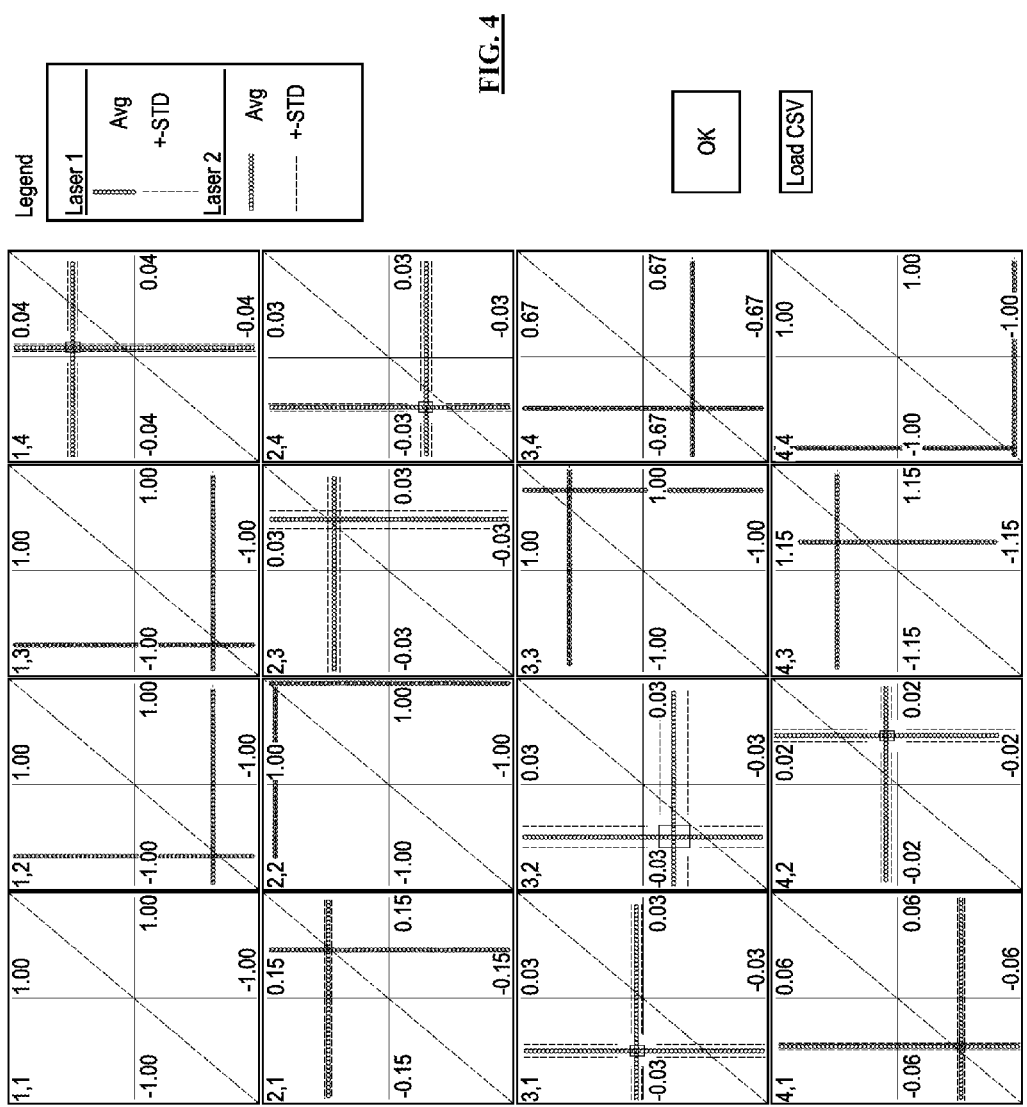
FIG. 4 is a schematic diagram illustrating a data output of dual Mueller matrices measured by the sensor of FIG. 2 according to the embodiments herein.

FIG. 4, with reference to FIGS. 1 through 3B, is an example of a dual Mueller matrix plot of data from bioaerosol protein chicken egg white albumen irradiated at beam wavelengths $(\lambda, \lambda^*) = (9.155, 10.458)$ μm. Normalized and averaged ordinate and abscissa of plots are $\mathcal{M}_{ij}(\lambda) = \langle M_{ij}(\lambda)/M_{11}(\lambda) \rangle$ and $\mathcal{M}'_{ij} = \langle M_{ij}(\lambda^*)/M_{11}(\lambda^*) \rangle$: respectively, the intersection of ordinate and abscissa open-dotted lines at $(\mathcal{M}_{ij}, \mathcal{M}'_{ij})$ are average values, and separation widths of paired ordinate and abscissa dashed lines are one standard deviations in $(\mathcal{M}_{ij}, \mathcal{M}'_{ij})$ datasets. Each M-element block contain domains. The rectangles given in blocks 1,4; 2,4; 3,1; 3,2; and 4,2 represent domains that lie furthest from the diagonal dashed line in that M-element block and are of particular interest. The perpendicular distance from coordinate $(\mathcal{M}_{ij}, \mathcal{M}'_{ij})$ to diagonal line is:

$$\rho_{ij} = 2^{1/2}[\mathcal{M}'_{ij}{}^2 + \mathcal{M}'_{ij}{}^2]^{1/2}\{\cos[\arctan(\mathcal{M}'_{ij}/\mathcal{M}_{ij})] - \sin[\arctan(\mathcal{M}'_{ij}/\mathcal{M}_{ij})]\} \quad (7)$$

where ij ∈ 1, 2, 3, 4 and ≠11. The quantities $|\rho_{ij}|$ from FIG. 4 are measures of susceptibility and a key identification parameter of bioaerosol protein. A multidimensional "detection domain" unique to the bioaerosol in Mueller matrix space can be built from between 1 and 15 $\rho_{ij}$ parameters and $(\mathcal{M}_{ij}, \mathcal{M}'_{ij})$ standard deviations modulo 2-beam wavelengths. Domains are sensor specific, as their size generally decreases as precision in M-elements measurement increases to a resolution limit: that limit is related to aerosol shape and Brownian motion in the beam cross section.

Figure 5:
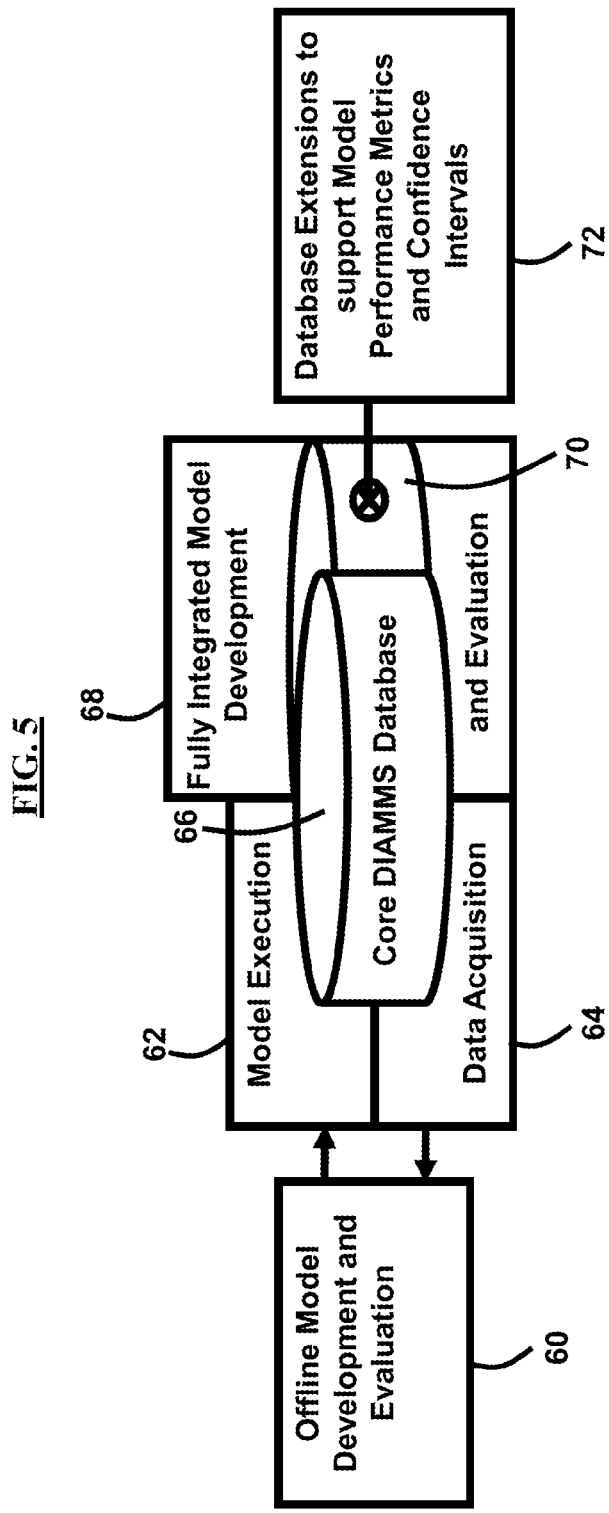
FIG. 5 illustrates a database production system and its processing according to the embodiments herein.

FIG. 5, with reference to FIGS. 1 through 4, is a block diagram illustrating a general overview of an interactive technique practiced for acquisition, processing, and analysis of M-elements empirical data (blocks 60-66) and integration of a best-performance decision support system (blocks 68-72) to the DIAMMS sensor (of FIG. 2). Self-organization maps (SOM) are artificial neural networks that utilize unsupervised competitive learning. A SOM, in effect, produces a non-linear mapping of attributes from high-dimensional feature space into a low-dimensional representation (typically two-dimensional for visualization purposes) while preserving topology. As acquired from the core database, a 32-dimension M matrix input space (16 M-element mean values and their standard deviations) of training samples is mapped into a two-dimensional map via the SOM. The resulting map is retrospectively color-coded based on the known aerosol type associated with each training record. A learning rate parameter governs the overall mapping action (clustering) and a conscience coefficient inhibits individual SOM nodes from winning too frequently.

Examples of software platforms for developing all hybrid Kohonen self-organizing map feed-forward artificial neural network models are the NeuralSight® software, the Neural Works Predict® software, and libraries supplied by the NeuralWare® company of Carnegie, Pa., USA. The NeuralSight® software is a high-throughput artificial neural network (ANN) model generator that automates structural and learning rule decisions in training SOM models while the NeuralWorks Predict® software utilizes an extensive library of mathematical transformations for producing inputs to the ANN multi-classifiers.

SOM architectures are currently specified manually. The multi-classifiers of aerosol aggregates comprise standard feed-forward ANNs trained using the gradient descent back-propagation algorithm and relative entropy as an internal fitness function. In this modeling effort, a wide variety of mathematical transformations from the NeuralWorks Predict® software operate on raw M-elements input vectors from the sensor. A genetic algorithm optimizer is executed, moreover, to identify the most promising variables for ANN training and validation. A method of cascade correlation training (within specified limits) is used to automatically determine nodes per dimension in the final architecture of candidate ANN classifiers.

Experimental results of SOM modeling from data in the core Mueller matrix knowledge repository—the middle infrared measurements of all 16 M-elements from nonviable γ-irradiated *Bacillus subtilis* and chicken egg white albumen analytes, Arizona road dust and water vapor interferents, and two talcum powders—are summarized in Table 2. Dimensions and number of epochs (passes through the dataset) for SOM maps varied in training the ANN classifier. In generating the results, 16 data fields (15 normalized non-[1, 1] M-elements plus the [1, 1] element) are clustered per aerosol spanning the 9.1-12.0 μm bandwidth of the sensor (of FIG. 2). All SOM maps are trained from the same dataset used to train the ANN classification models. SOM training may be terminated after 20,000 iterations through an M-elements dataset comprising 1,560 records (all aerosols). Table 2 summarizes the classification model performance metrics of the SOM.

TABLE 2

| | Accuracy (%) | BS | EGG | WV | BT | ARD | MT | Total |
|---|---|---|---|---|---|---|---|---|
| Modeling | | | | | | | | |
| Bacillus subtilis | 100.0% | 318 | 0 | 0 | 0 | 0 | 0 | 318 |
| Egg Albumen | 100.0% | 0 | 324 | 0 | 0 | 0 | 0 | 324 |
| Water Vapor | 100.0% | 0 | 0 | 230 | 0 | 0 | 0 | 230 |
| Baby Talc | 100.0% | 0 | 0 | 0 | 297 | 0 | 0 | 297 |

TABLE 2-continued

| | Accuracy (%) | BS | EGG | WV | BT | ARD | MT | Total |
|---|---|---|---|---|---|---|---|---|
| Arizona Road Dust | 100.0% | 0 | 0 | 0 | 0 | 321 | 0 | 321 |
| Mineral Talc | 100.0% | 0 | 0 | 0 | 0 | 0 | 70 | 70 |
| Total Average Validation | 100.0% 100.0% | 318 | 324 | 230 | 297 | 321 | 70 | 1560 |
| *Bacillus subtilis* | 100.0% | 106 | 0 | 0 | 0 | 0 | 0 | 106 |
| Egg Albumen | 100.0% | 0 | 108 | 0 | 0 | 0 | 0 | 108 |
| Water Vapor | 100.0% | 0 | 0 | 34 | 0 | 0 | 0 | 34 |
| Baby Talc | 100.0% | 0 | 0 | 0 | 99 | 0 | 0 | 99 |
| Arizona Road Dust | 100.0% | 0 | 0 | 0 | 0 | 107 | 0 | 107 |
| Mineral Talc | 100.0% | 0 | 0 | 0 | 0 | 0 | 24 | 24 |
| Total Average | 100.0% 100.0% | 106 | 108 | 34 | 99 | 107 | 24 | 478 |

The embodiments herein provide a robust approach to the identification and standoff detection of toxic biological aerosol threats based on DIAMMS and ANN analytics was demonstrated in the laboratory. However, the transition of DIAMMS technology to a field able tactical sensor must fulfill certain requirements for success. Among these are demonstrating the capabilities of DIAMMS to: (i) characterize threat agents in situ at safe distances by type and (if possible) quantity with minimum false positives/negatives: (ii) mitigate contaminant threat and produce guidance in evacuating areas of danger: and (iii) aid in establishing contamination avoidance perimeters.

A representative hardware environment for practicing the embodiments herein is depicted in FIG. 6, with reference to FIGS. 1 through 5. This schematic drawing illustrates a hardware configuration of an information handling/computer system 100 in accordance with the embodiments herein. The system 100 comprises at least one processor or central processing unit (CPU) 110. The CPUs 110 are interconnected via system bus 112 to various devices such as a random access memory (RAM) 114, read-only memory (ROM) 116, and an I/O adapter 118. The I/O adapter 118 can connect to peripheral devices, such as disk units 111 and tape drives 113, or other program storage devices that are readable by the system 100. The system 100 can read the inventive instructions on the program storage devices and follow these instructions to execute the methodology of the embodiments herein. The system 100 further includes a user interface adapter 119 that connects a keyboard 115, mouse 117, speaker 124, microphone 122, and/or other user interface devices such as a touch screen device (not shown) to the bus 112 to gather user input. Additionally, a communication adapter 120 connects the bus 112 to a data processing network 125, and a display adapter 121 connects the bus 112 to a display device 123 which may be embodied as an output device such as a monitor, printer, or transmitter, for example.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An active spectrophotopolarimeter sensor and support system for distant chemical and biological aerosol and surface contamination standoff detection, comprising:
    a grating-tunable, continuous-wave, linearly polarized, $CO_2$ laser system producing beam outputs comprising an isotopic admixture of $CO_2$ gas in a gain medium of a laser providing a tunable bandwidth of a spectrophotopolarimeter sensor and double spectral selectivity;
    an optomechanical switch that produces an alternate square-wave train of incident beam pulses as output, measures power of the beam outputs when directed to an internal detector, and determines a wavelength of beams when directed to a pair of optical spectrum analyzers;
    a coupled transmitter linear polarizer and photoelastic modulator optic pair (POL-PEM) with 45° alignment of axes, mated to a precision rotary stage with computer-driven stepper motor control, and operating on irradiance from the incident beam pulses;
    telescope spider and mirror mounts that direct said alternate square-wave train of incident beam pulses onto an aerosol aggregate;
    a collimator and telescopic receiver operatively connected to said telescope spider and mirror mounts;
    a coupled receiver photoelastic modulator and linear polarizer optic pair (PEM-POL) with 45° alignment of axes, mated to a precision rotary stage with computer-driven stepper motor control, and operating on backscattering beam outputs;
    a variable neutral density filter disk with belt-driven servo feedback control for regulation of backscattered radiances; and
    a parabolic mirror focusing collimated radiance of beam outputs onto a cooled HgCdTe photoconductive chip detector.

2. The active spectrophotopolarimeter sensor and support system of claim 1, wherein said chip detector is cooled at a liquid nitrogen temperature of approximately 77K.

3. The active spectrophotopolarimeter sensor and support system of claim 1, further comprising a computerized artificial neural network model developed based on the statistics of said bioaerosol as a classifier database of aerosol aggregates.

4. The active spectrophotopolarimeter sensor and support system of claim 3, wherein said artificial neural network model comprises a hybrid Kohonen self-organizing map (SOM) feed-forward artificial neural network model.

5. An apparatus for dissemination, confinement, and size/concentration measurements of aerosols comprising a bioaerosol, said apparatus comprising:
    an enclosed chamber comprising said aerosols;
    a pair of entrance/exit apertures comprising shutters that open/close said apertures;
    an aerosol intake port operatively connected to said chamber;
    an aerodynamic particle sizer operatively connected to said aerosol intake port;
    a high-pressure ejection nozzle operatively connected to said chamber;

a hopper and aerosol reservoir that provides powder samples to said chamber through said nozzle;

a plurality of conduits that control aerosol movement to/from said chamber;

a vacuum switch operatively connected to said plurality of conduits, wherein said vacuum switch controls exhaust of said bioaerosol from said chamber via said plurality of conduits; and a chamber vacuum cleaner operatively connected to said chamber.

6. The apparatus of claim 5, further comprising:

a spectrophotopolarimeter comprising a sensor receiver;

a system that aligns said spectrophotopolarimeter to said chamber, inspects a uniformity of a dispersed aerosol sample inside said chamber, and measures a particle size distribution and concentration of a sampling plume of said bioaerosol;

a visible HeNe laser beam on-axis of said sensor receiver;

a plurality of flat mirrors aligned outside opposing walls of said chamber, wherein said mirrors reflect said visible HeNe laser beam in a Z-pattern for direct inspection of particle scattering and vertical aerosol density; and a console system operatively connected to said aerodynamic particle sizer that processes and displays statistics of said bioaerosol.

7. The apparatus of claim 6, wherein said spectrophotopolarimeter comprises:

a grating-tunable, continuous-wave, linearly polarized, $CO_2$ laser system producing beam outputs comprising an isotopic admixture of $CO_2$ gas in a gain medium of a laser providing a wider tunable bandwidth of a spectrophotopolarimeter sensor and double spectral selectivity;

an optomechanical switch that produces an alternate square-wave train of incident beam pulses as output, measures power of the beam outputs when directed to an internal detector, and determines a wavelength of beams when directed to a pair of optical spectrum analyzers;

a coupled transmitter linear polarizer and photoelastic modulator optic pair (POL-PEM) with 45° alignment of axes, mated to a precision rotary stage with computer-driven stepper motor control, and operating on irradiance from the incident beam pulses;

telescope spider and mirror mounts that direct said alternate square-wave train of incident beam pulses onto an aerosol aggregate; and a collimator and telescopic receiver in a Cassegrain style operatively connected to said telescope spider and mirror mounts.

8. The apparatus of claim 7, wherein said spectrophotopolarimeter further comprises:

a coupled receiver photoelastic modulator and linear polarizer optic pair (PEM-POL) with 45° alignment of axes, mated to a precision rotary stage with computer-driven stepper motor control, and operating on backscattering beam outputs;

a variable neutral density filter disk with belt-driven servo feedback control for regulation of backscattered radiances; and a parabolic mirror focusing collimated radiance of beam outputs onto a cooled HgCdTe photoconductive chip detector.

9. The apparatus of claim 8, wherein said chip detector is cooled at a liquid nitrogen temperature of approximately 77K.

10. The apparatus of claim 6, further comprising a computerized artificial neural network model developed based on the statistics of said bioaerosol as a classifier database of aerosol aggregates.

11. The apparatus of claim 10, wherein said artificial neural network model comprises a hybrid Kohonen self-organizing map (SOM) feed-forward artificial neural network model.

12. The apparatus of claim 5, further comprising:

an inner tube aligned with said pair of entrance/exit apertures; and a vapor mist concentration generator positioned within said chamber and aligned with said inner tube.

13. The apparatus of claim 5, wherein said chamber is windowless.

14. The apparatus of claim 5, wherein said plurality of conduits comprise:

a low vacuum conduit used prior to high-efficiency particulate air (HEPA) filtration of said chamber for containment of said bioaerosol within said chamber;

a first high vacuum conduit used prior to said HEPA filtration of said chamber for evacuation of said bioaerosol; and a second high vacuum conduit used subsequent to HEPA filtration for ventilation of said chamber.

15. The apparatus of claim 5, further comprising a pair of gloves operatively insertable inside said chamber and used for washing the inside of said chamber.

16. A method of generating Stokes vectors, a Mueller matrix, and polarized scattering from an aerosol aggregate, said method comprising:

providing an incident infrared laser beam;

causing said incident infrared laser beam to be polarization-modulated using variable stress/strain birefringence imposed on a ZnSe crystal;

defining a Stokes vector associated with said incident infrared laser beam;

scattering said incident infrared laser beam from an aggregate aerosol comprising interferents and analyte particles;

producing a scattered-beam reactant Stokes vector by causing the scattered incident infrared laser beam to be polarization-modulated;

generating a Mueller matrix by taking a transformation of said Stokes vector; and identifying said analyte using said Mueller matrix:

17. The method of claim 16, wherein said Mueller matrix comprises M-elements that are functions of a wavelength of said infrared laser beam, backsattering orientation of said infrared laser beam, and a shape and size of said interferents and analyte particles.

18. The method of claim 16, further comprising:

directing a pair of continuous-wave $CO_2$ laser beams into entrance ports of an optical switching device, wherein an output of said optical switching device comprises an alternate square-wave sequence of equal intensity laser beams;

directing said equal intensity laser beams into optical spectrum analyzers for wavelength determination;

directing said equal intensity laser beams through a coupled linear polarizer-then-photoelastic modulation (POL-PEM) optics unit; and confining a temporal transverse electromagnetic wave of said equal intensity laser beams to a given geometric plane to establish a Stokes vector associated with a polarization state of said equal intensity laser beams.

19. The method of claim 18, further comprising:
modulating said Stokes vector via periodic stress/strain birefringence transduction;
creating a polarization-modulated laser beam from said POL-PEM optics unit;
reflecting said polarization-modulated laser beam twice 90° using flat mirrors;
directing the reflected laser beam into an aerosol chamber comprising entrance and exit apertures centered on-axis with a spectrophotopolarimeter receiver; and
collecting backscattered radiance of said reflected laser beam scattered from said bioaerosols using a coupled linear photoelastic-then-polarizer modulation (PEM-POL) optics unit.

20. The method of claim 18, further comprising splitting a portion of said equal intensity laser beams into a power meter head unit.

21. The method of claim 16, further comprising developing an artificial neural network model based on the identified analyte as a classifier database of aerosol aggregates.

22. The method of claim 21, wherein said artificial neural network model comprises a hybrid Kohonen self-organizing map (SOM) feed-forward artificial neural network model.

* * * * *